United States Patent
Leonhardt

[11] Patent Number: 6,149,575
[45] Date of Patent: Nov. 21, 2000

[54] RADIATION DELIVERY CATHETER

[75] Inventor: Howard J. Leonhardt, Davie, Fla.

[73] Assignee: World Medical Manufacturing Corporation, Sunrise, Fla.

[21] Appl. No.: 09/111,421

[22] Filed: Jul. 7, 1998

[51] Int. Cl.[7] ............................ A61B 5/00; A61M 29/00
[52] U.S. Cl. ................ 600/4; 600/1; 600/3; 604/96; 604/97; 604/101
[58] Field of Search .................. 600/3, 4, 5, 1; 606/191, 192, 194; 604/96, 97, 101, 104

[56] References Cited

U.S. PATENT DOCUMENTS

| | | | |
|---|---|---|---|
| 5,290,306 | 3/1994 | Trotta et al. | 606/194 |
| 5,358,486 | 10/1994 | Saab | 604/96 |
| 5,536,252 | 7/1996 | Imran et al. | 604/101 |
| 5,540,659 | 7/1996 | Teirstein | 604/104 |
| 5,613,979 | 3/1997 | Trotta et al. | 606/194 |
| 5,707,332 | 1/1998 | Weinberger | 600/3 |
| 5,879,282 | 3/1999 | Fischell et al. | 600/3 |
| 5,913,813 | 6/1999 | Williams et al. | 600/3 |

Primary Examiner—Cary O'Connor
Assistant Examiner—Navin Natnithithadha
Attorney, Agent, or Firm—Sterne, Kessler, Goldstein & Fox P.L.L.C.

[57] ABSTRACT

A radiation delivery catheter with inflatable chambers which provide a layer of radiation of minimum effective dose possible to be delivered as close as possible to the origin of disease within a blood vessel. The device can be centered within the true lumen of a vessel to provide even dispersion of the radiation agent to the outer wall of the vessel. The catheter comprises two central self centering balloons, one thin radiation agent inflatable chamber, and one radiation spread cloaking inflatable chamber with high strength properties resistant to rupture.

21 Claims, 1 Drawing Sheet

RADIATION DELIVERY CATHETER

FIELD OF THE INVENTION

The present invention relates to the field of radiation delivery apparatus. More particularly, this invention provides an apparatus for delivery of controlled doses of radiation to diseased blood vessels. This device is useful for reducing the rate of restenosis of diseased blood vessels without any significant side effects.

BACKGROUND OF THE INVENTION

Cardiovascular disease is the leading cause of deaths in the industrialized world. Most cardiovascular related deaths are caused by blockage of blood flow in stenotic (narrowed) vessels. The primary cause of narrowing of vessels is the build up of plaque. A common treatment for narrowed blood vessels is deployment of devices like balloon catheters or metallic stents that push the plaque against the wall of the vessel. A commonly used technique for treating coronary artery obstruction is percutaneous transluminal coronary angioplasty (hereinafter referred to as "PTCA") and involves insertion of balloon catheters through the femoral artery to the targeted coronary artery. Injection of radio-opaque contrast into the proximal coronary artery allows fluoroscopic localization of the blocked coronary segments. Balloon catheters are advanced to the site of stenosis over thin guide wires to position the catheter at the point of blockage. The distal end of the catheter contains a balloon which is inflated to press the plaque against the wall of the artery.

A common problem following PTCA is reclosure of the blood vessel. This phenomenon, known as restenosis, is thought to result from intimal hyperplasia of the vessel, in part due to proliferation of smooth muscle cells. Generally, 33%. of balloon angioplasty and metallic stent treatments result in restenosis, which is usually observed within one year of the procedure.

Recently, researchers have begun the use of radiation to inhibit smooth muscle cell proliferation. It has been shown that intracoronary delivery of ionizing radiation causes focal medial fibrosis, which when delivered at the site of the angioplasty, impedes the restenosis process. By carefully selecting the type of radiation, adjacent structures and vessels are undamaged by the radiation.

Currently available devices include radioactive wires or stents, and balloon-less catheters containing radiation pellets. Wire-less, balloon-less radiation pellets have several disadvantages. Centering of the device within the lumen of the vessel is difficult to achieve resulting in delivery of uneven doses of radiation to the entire segment of the vessel wall. These pellets often lay on one side of the vessel and burn that side resulting in necrosis without providing adequate radiation to the other side of the vessel. In addition, there is a danger of loss of pellets from the delivery system. Furthermore, the wire and balloon-less catheter systems also irradiate the entire vessel, even the areas which do not require treatment. Uncontrolled doses of radiation in normal non-stenotic vessels can actually cause proliferation of smooth muscles and other side effects. Radioactive stents and wires that are intended to be left in the vessel for an extended period of time may cause more intimal hyperplasia than ordinary non-irradiated stents. While the radioactive stents and wires may be centered, they are likely to be centered within the off center lumen created by the diseased state rather than the true lumen of the vessel. Again, this may result in uneven delivery of radiation dose to the blood vessel wall.

Thus, there is an ongoing need for devices that can be positioned correctly within the lumen of the blood vessels to reduce the rate of restenosis without major side effects.

SUMMARY OF THE INVENTION

The present invention provides a radiation delivery catheter with inflatable chambers which are equipped with a layer of radiation for delivery of an effective dose of radiation as close as possible to the origin of the disease within a blood vessel. The device comprises a multi-lumen catheter with multiple lumen extensions and pressure release valves. At the tip of the catheter are overlapping balloons or inflatable chambers. The centermost balloon is divided into two sections. An outer balloon is filled with radioactive material. The device is also equipped with another balloon wrapped around the outer balloon that forms a controlled cloaking layer that allows the device to be cloaked while being deployed. An operator can release the radiation when desired at the target location and also re-cloak the radiation for removal of the device. Means are also provided for the flow of blood through a channel in the catheter so as to bypass the radiation delivery mechanism. This device may be used in combination with an balloon angioplasty and/or stent placement balloon. Also, a miniature radiation dose sensor may be placed on the catheter to monitor the dose of radiation delivered to the surrounding vessel wall.

To use the device the multi-lumen catheter system is inserted into a patient in a conventional manner. The distal end of the catheter containing the balloons is guided to the desired spot in the vasculature. Upon positioning of the catheter in the desired location, a radioactive material is delivered via a lumen extension to a balloon. A radioprotective material is delivered at the same time to a balloon exterior to the radiation balloon. A shunt in the catheter allows for bypass of the blood while radiation is being delivered to the wall of the blood vessel.

Accordingly, it is an object of the present invention to provide a device for reducing the incidence of restenosis.

Another object of the invention is to provide a device for reducing the incidence of restenosis by delivery of precise dose of radiation to the blocked artery at the blockage area.

A still further object of the present invention is to provide a device for the delivery of radiation to a target in the vascular system without unnecessary exposure to other areas of the body.

A yet another object of the present invention is to provide a device for the delivery of radiation to a blocked blood vessel wall with a shunt for the bypass of fluids.

These and other objects of the invention, the novel features of the invention and the manner of using the invention will be best understood from the accompanying drawings in conjunction with the specifications.

DETAILED DESCRIPTION OF THE PREFERRED EMBODIMENT

Figure 1:
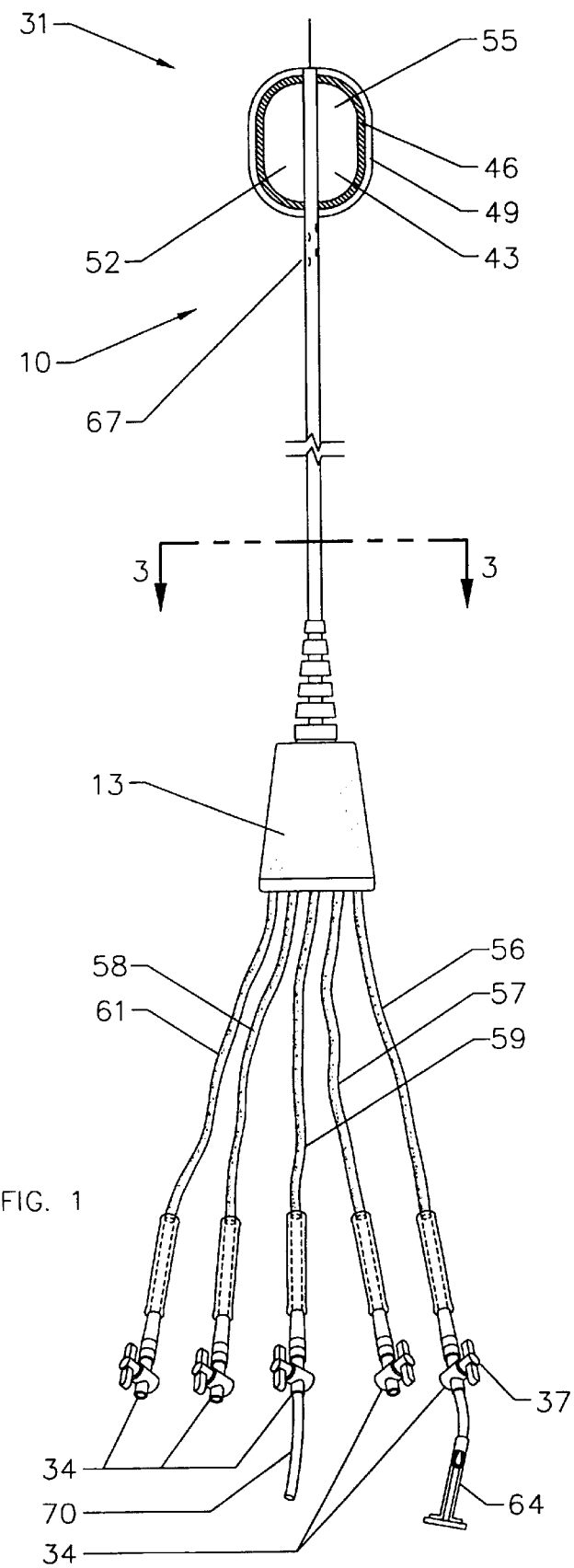
FIG. 1 is a perspective view of the radiation delivery catheter of the present invention.
Figure 3:
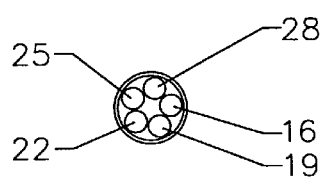
FIG. 3 is a sectional view taken along line 3—3 of FIG. 1.
Figure 2:
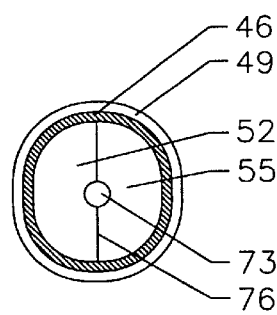
FIG. 2 is a partial end view of the radiation delivery catheter of the present invention.

Referring to FIGS. 1–3 generally and initially referring to FIG. 1, a catheter 10 has a junction 13 where multiple lumens 16, 19, 22, 25, and 28 (shown in FIG. 3) converge. The catheter 10 has a distal end 31 that is sized to be capable of being introduced into the vascular system of the human body percutaneously through the Seldinger technique and the like, as will be apparent to those of ordinary skill in the art. The catheter 10 is elongate and narrow and preferably formed out of plastic. The lumens 16, 19, 22, 25 are disposed inside the catheter 10 on the distal side of the junction 13. Lumen extensions 56, 57, 58, 59, and 61 are disposed on the outside of the catheter on the other side of the junction 13.

On the side of the junction 13 opposite the distal end 31, the lumen extensions 56, 57, 58, 59, and 61 are attached to stopcocks 34 that provide for opening and closing the flow into the lumens. The stopcocks 34 are also provided with pressure relief valves 37 the function of which will be described below.

At the distal end 31 of the catheter 10, a balloon 43, a first inflatable chamber 46, and a second inflatable chamber 49 provide for delivering radiation to a specific area inside a blood vessel. The balloon 43 is preferably constructed of a compliant, soft durometer plastic such as, but not limited to, 80A Pellethane polyurethane. The balloon 43 is preferably divided into two compartments 52 and 55. The compartments 52 and 55 are capable of being inflated with an inert solution such as saline or the like.

The first inflatable chamber 46 is wrapped around the balloon 43. The chamber 46 is hollow and preferably completely surrounds the balloon 43. In this manner, once the catheter 10 is positioned correctly within the lumen of the blood vessel, the inflation of the balloon 43 causes the chamber 46 to be uniformly pressed against the interial walls of the blood vessel. The chamber 46 is preferably constructed of an elastic material that is resistant to rupture such as, but not limited to, a high durometer polyurethane and the like. Once the catheter 10 is positioned inside the lumen of the blood vessel as described above, a radioactive material (not shown) is introduced into lumen 19 through lumen extension 58. With the chamber 46 pressed against the vessel wall by the balloon 43, the chamber 46 conforms to the shape of the vessel wall to provide an even dispersion about 360 degrees to the vessel adventia without necrosis. Injection holes (not shown) for inflating the chamber 46 are disposed above and below the edges of the balloon compartments 52 and 55.

The second inflatable chamber 49 is wrapped around and preferably completely surrounds the first chamber 46. The second inflatable chamber 49 is constructed of a high strength plastic material that is resistant to rupture. The second inflatable chamber 49 is capable of being inflated with a cloaking cover agent that inhibits the spread of radiation from the first chamber 46. An agent such as a graphite solution, low viscosity contrast media, liquid Lucite or any other non-toxic agent that blocks the spread of radiation and particularly Beta emitting radiation is introduced into lumen 16 through lumen extension 61. This chamber 49 provides a shield or cloak for preventing the spread of radiation when the catheter 10 is being removed and also provides a shield in the event that the first chamber 46 ruptures.

The pressure relief valves 37 that are connected to the stopcocks 34 also provide a measure of security against a rupture of the chambers 46 and 49 due to too much pressure build up. The lumen extensions 56, 57, 58, and 61 are preferably filled by controlled, fixed volume syringes 64. If the plunger on the syringe 64 causes too much pressure build up inside the lumens, the pressure relief valve 37 will open to prevent the balloon 43 or the chambers 46 and 49 from rupturing.

The catheter 10 is equipped with a set of openings 67 on the side of the catheter 10 opposite the distal end 31. The openings 67 provide for perfusion of the blood vessel beyond the treatment site in the event that the treatment time exceeds a few minutes.

The catheter 10 accommodates a standard guide wire 70 for placement with the standard percutaneous techniques. Also, the catheter 10 can accommodate an intravascular ultrasound probe to allow for visualization of the vessel for more control of the centering of the device. For monitoring purposes, the catheter 10 can be equipped with a miniature radiation dose sensor at the distal end 31. In order to combine treatments, the catheter 10 could be equipped with an angioplasty balloon or a stent placement balloon for opening the vessel wall prior to the radiation treatment.

Turning to FIG. 2, a perfusion channel 73 is disposed along the center of the catheter 10. A dividing member 76 divides the balloon 43 into compartments 52 and 55.

In operation, the multi-lumen catheter 10 is inserted into the vascular system of a patient in a conventional manner known to those skilled in the art. The distal end 31 of the catheter 10 containing the balloon 43 and the inflatable chambers 46 and 49 are guided to the desired position in the vasculature. Upon positioning of the catheter 10 in the desired location by inflation of the compartments 52 and 55 of the balloon 43, the radioactive material is delivered via the lumen extension 58 to the first chamber 46. The perfusion openings 67 provide for bypass of the blood while radiation is being delivered uniformly to the inner wall of the blood vessel by the radioactive material in the first chamber 46. The uniform application of the radiation equally around the entire periphery of the vessel wall reduces the possibility of necrosis occurring from an unbalanced dosage of radiation and provides the best method of delivering radiation to the outer wall or adventia of the blood vessel.

Once the radiation treatment has been concluded, the balloon 43 and the first chamber 46 are deflated and the second chamber 49 is inflated. Inflation of the second chamber 49 provides a cloak or shield to prevent the spread of radiation to areas of the body other than the treatment site. Filling the second chamber 49, which completely surrounds the first chamber 46, with radiation blocking materials provides the shielding effect. Once the second chamber 49 is filled, the catheter 10 and the guide wire 70 can be removed through the percutaneous opening and the entry site can be attended to.

Accordingly, the present invention provides several advantages. The device can deliver a precise dosage of radiation and deliver it uniformly around the inside wall of a blood vessel. Also, by introducing the radiation through a lumen after the catheter 10 has been positioned, the potential for spreading radiation to unintended areas of the body while the catheter 10 is en route to the targeted area is eliminated. Also, the shielding chamber 49 prevents the spread of radiation once the treatment has been concluded and the catheter 10 is being removed. The uniform dispersion of radiation made possible by centering the device inside the true vessel lumen (not the lumen created by the disease) and by pressing the first chamber 46 against the inside of the vessel wall around the full 360 degrees, reduces the occurrence of necrosis and facilitates treatment of the outer walls of the blood vessel.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

What is claimed is:

1. A catheter tip, comprising:
   a) a balloon;
   b) a first inflatable chamber disposed around the balloon and capable of being fluidly connected to a first lumen of a catheter; and
   c) a second inflatable chamber disposed around the first inflatable chamber and capable of being fluidly connected to a second lumen of the catheter.

2. The catheter tip of claim 1, wherein the first inflatable chamber completely surrounds the balloon.

3. The catheter tip of claim 1, wherein the second inflatable chamber completely surrounds the first inflatable chamber.

4. The catheter tip of claim 1, wherein the balloon is divided into two compartments.

5. The catheter tip of claim 1, further comprising:
   a lumen having a plurality of openings capable of providing for perfusion of a blood vessel.

6. A catheter tip of claim 1, wherein the first inflatable chamber is capable of being inflated with a radiation emitting substance.

7. The catheter tip of claim 1, wherein the second inflatable chamber is capable of being inflated with a substance capable of inhibiting the spread of radiation.

8. A radiation delivery apparatus for delivering radiation to a blood vessel having a lumen and a vessel wall, the radiation delivery apparatus, comprising:
   a catheter having a plurality of lumens and having a distal end;
   at least one balloon disposed at the distal end of the catheter and connected to one of the plurality of lumens;
   a first inflatable chamber disposed around the balloon and connected to one of the plurality of lumens;
   a second inflatable chamber disposed around the first chamber and connected to one of the plurality of lumens; and
   a guide wire disposed inside the catheter through one of the plurality of lumens.

9. The apparatus of claim 8, wherein the at least one balloon is divided into two compartments.

10. The apparatus of claim 8, wherein the catheter has a plurality of openings to provide for perfusion of the blood vessel.

11. The apparatus of claim 8, further comprising:
    a radiation dose sensor disposed at the distal end of the catheter.

12. The apparatus of claim 8, further comprising:
    a controlled fixed volume syringe connected to one of the plurality of lumen such that a substance from inside the syringe is capable of passing through at least one of the plurality of lumen.

13. The apparatus of claim 8, further comprising:
    a plurality of valves connected to the plurality of lumens such that flow into the at least one balloon, the first inflatable chamber, and the second inflatable chamber is capable of being controlled.

14. The apparatus of claim 13, further comprising:
    a pressure relief valve connected to at least one of the plurality of valves.

15. The apparatus of claim 8, further comprising:
    an intravascular ultrasound probe capable of being disposed through one of the plurality of lumen into the blood vessel.

16. The apparatus of claim 8, further comprising:
    an angioplasty balloon disposed at the distal end of the catheter.

17. The apparatus of claim 8, further comprising:
    a stent placement balloon disposed at the distal end of the catheter.

18. The apparatus of claim 8, wherein the first inflatable chamber is capable of extending lengthwise.

19. The apparatus of claim 8, wherein the second inflatable chamber is capable of extending lengthwise.

20. A radiation delivery apparatus for delivering radiation to a diseased blood vessel having a lumen and a vessel wall, the radiation delivery apparatus, comprising:
    a catheter having a plurality of lumens and having a distal end;
    means for providing radiation to the wall of the diseased blood vessel;
    means for pressing the radiation means against the vessel wall;
    means for centering the catheter inside the lumen of the blood vessel;
    means for shielding the radiation means during deployment and removal of the catheter; and
    means for conveying substances through the plurality of lumens to the radiation means, pressing means, and shielding means.

21. A method of delivering radiation to a lumen of a diseased blood vessel, comprising the steps of:
    providing a radiation delivery apparatus for delivering radiation to a blood vessel having a lumen and a vessel wall, the radiation delivery apparatus, comprising: a catheter having a plurality of lumens and having a distal end; at least one balloon disposed at the distal end of the catheter and connected to one of the plurality of lumens; a first inflatable chamber disposed around the balloon and connected to one of the plurality of lumens; a second inflatable chamber disposed around the first chamber and connected to one of the plurality of lumens; and a guide wire disposed inside the catheter through one of the plurality of lumens; to form a radiation delivering balloon catheter;
    inserting the guide wire percutaneously through the femoral artery and retrieving the guide wire through a predetermined upper artery;
    deploying the radiation delivering balloon catheter along the guide wire to the lumen of the diseased blood vessel;
    inflating the balloon with an inert solution to center the catheter inside the lumen of the blood vessel;
    inflating the first inflatable chamber by filling the chamber with a radiation emitting substance;
    inflating the balloon to press the first inflatable chamber against the vessel wall;
    providing radiation to the diseased blood vessel for a predetermined amount of time;
    inflating the second inflatable chamber by filling the chamber with a substance capable of inhibiting the spread of radiation;
    deflating the balloon and the first inflatable chamber; and
    removing the radiation delivering balloon catheter and the guide wire from the blood vessel.

* * * * *